United States Patent [19]

Grigoleit et al.

[11] 3,991,074

[45] Nov. 9, 1976

[54] PROCESS FOR THE CATALYTIC CONVERSION OF o-ETHYLANILINE TO INDOLE

[75] Inventors: Georg Grigoleit; Gerd Collin; Rudolf Oberkobusch, all of Duisburg-Meiderich, Germany

[73] Assignee: Rutgerswerke Aktiengesellschaft, Frankfurt am Main, Germany

[22] Filed: Nov. 15, 1974

[21] Appl. No.: 524,290

Related U.S. Application Data

[63] Continuation-in-part of Ser. No. 354,411, April 25, 1973, abandoned.

[30] Foreign Application Priority Data

Jan. 10, 1974 Germany............................ 2401017

[52] U.S. Cl.............................. 260/319.1; 252/457
[51] Int. Cl.².......................................... C07D 209/10
[58] Field of Search................................. 260/319.1

[56] References Cited
UNITED STATES PATENTS

| | | | |
|---|---|---|---|
| 3,652,674 | 3/1972 | Hansen et al. | 260/586 A |
| 3,773,784 | 11/1973 | Mauri et al. | 260/319.1 |

*Primary Examiner*—Lewis Gotts
*Assistant Examiner*—S. P. Williams
*Attorney, Agent, or Firm*—Beveridge, DeGrandi, Kline, Lunsford

[57] ABSTRACT

A process for the catalytic conversion of o-ethylaniline to indole in a gaseous phase and in the presence of hydrogen or steam and an $SiO_2$-containing catalyst modified by chromium dioxide and copper, wherein said conversion is conducted at about 400° – 700° C.; said catalyst comprising at least about 15% by weight copper and at least about 8% by weight of a chromate of a metal of Group IIA of the Periodic Table. A catalyst for use in the invention is provided.

9 Claims, No Drawings

PROCESS FOR THE CATALYTIC CONVERSION OF O-ETHYLANILINE TO INDOLE

This application is a continuation-in-part of application Ser. No. 354,411, filed Apr. 25, 1973, now abandoned, the entire disclosure of which is relied upon and incorporated herein by reference.

This invention relates to a process for the production of indole from o-ethylaniline in the presence of a catalyst.

It is known in the art that indole can be produced by the dehydrocyclization of o-ethylaniline in a gaseous phase. According to known processes, conversion in the gaseous phase is carried out in the presence of a catalyst containing an activated $Al_2O_3$ or an activated $SiO_2$. These catalysts can optionally be modified with oxides of multivalent metals, such as the oxides of chromium, copper, cobalt, molybdenum or vanadium. They can also be modified with noble metal catalysts, such as platinum or palladium. Titanium dioxide can also be used as a modifier.

According to these known processes, o-ethylaniline is reacted in a gaseous phase in the presence of hydrogen, nitrogen or air, and in the presence of a dehydration catalyst (for example $Al_2O_3$ or $SiO_2$), at temperatures between 400° and 700° C. In the prior art processes, it is preferred to modify the catalyst with the aforementioned metal oxides or noble metals. The yield of indole obtained from these known processes is between 20 and 60% of the theoretical yield. These known processes for indole synthesis have not proved entirely satisfactory for industrial application because of these relatively low yields.

Accordingly, there has been a need in the art for a process for the production of indole from o-ethylaniline in a gaseous phase, and in the presence of a catalyst.

It has now been found that the yield of indole from the catalytic conversion of o-ethylaniline can be increased very significantly if the proportion of copper in a chromium-copper catalyst is increased beyond the amount customarily employed in known processes, and further if a chromate of a metal of Group IIA is included in the catalyst.

Accordingly, this invention provides a process for the catalytic conversion of o-ethylaniline to indole in a gaseous phase, and in the presence of hydrogen or steam and an $SiO_2$—containing catalyst. The conversion is conducted at about 400° – 700° C. The catalyst is modified with chromium dioxide and copper, and comprises at least about 15% by weight of the copper, and also at least about 8% by weight of a chromate of a metal of Group IIA of the Periodic Table. Preferably, the chromate of the metal of Group IIA is barium chromate.

In a preferred embodiment of this invention, the catalyst comprises about 55 – 65% by weight $SiO_2$, about 18 – 24% by weight copper, about 8 – 10% by weight barium chromate and about 2 – 4% by weight chromium dioxide.

According to the process of this invention, indole can be produced by a conversion of 51% of the o-ethylaniline, at yields of about 85% of the theoretical yield, and practically without the production of by-products. Such a yield is considerably above that obtainable by the prior art processes.

The process of this invention is preferably carried out by evaporating the o-ethylaniline, keeping the resulting vapor stream at the desired reaction temperature, and then admixing steam or preheated hydrogen with the vapor stream immediately prior to contacting the stream with the catalyst bed. The reaction can be conducted over a wide temperature range, typically about 400° – 700° C. Preferably, the reaction temperature is about 500° – 600° C.

The contact time of the vapor stream with the catalyst bed can vary over a wide range. Usually, it is not necessary to exceed 5 seconds at standard pressure and reaction temperature. It will be understood that the contact time varies with the reaction temperature and specific volume of the catalyst. For the preferred catalyst used in practicing the process of this invention, a contact time of about 3 – 5 seconds is preferred.

The space velocity of the reactants, i.e., the parts by volume of the mixture of o-ethylaniline vapor and hydrogen, flowing through the reactor per unit volume of the catalyst per hour, is preferably about 100 – 1500 reciprocal hours.

It will also be understood that the mole ratio of o-ethylaniline to hydrogen can be varied over a wide range. Typically, this range is about 1:4 – 1:20. The ratio is preferably about 1:4 – 1:8.

The process of this invention can be carried out in a solid, fluidized or fluid bed.

The product of the process of this invention is indole, and can be separated from unconverted o-ethylaniline by conventional techniques. For example, indole can be separated from the reaction mixture by fractional distillation or extraction with a suitable solvent. The o-ethylaniline separated from the indole can then be recycled to the process.

This invention will be more clearly understood by reference to the Examples which set forth preferred embodiments of this invention. All parts, proportions, percentages and ratios are by weight unless otherwise indicated. Example 2 is included for purposes of comparison of the process of this invention with a process disclosed at J. Am Chem. Soc. 73, 3080 (1951) or Roczniki Chemii 31, 1057 (1957).

EXAMPLE 1

60.5 g (½ mole) o-ethylaniline are fed over a period of 2 hours into an evaporator by means of a metering pump, and evaporated. At the same time, 67.2 Nl hydrogen are fed by a metering apparatus to a preheat zone of a glass reactor, where mixing with the o-ethylaniline vapors at a temperature of 500° C occurs.

The gas mixture is contacted in the reactor with 200 ml of an $SiO_2$-containing catalyst heated to 550° C. The catalyst is previously modified with 22% by weight of copper, 8% by weight of barium chromate and 2% by weight of chromium dioxide.

The space velocity is 196 h$^{-1}$, the time of direct contact is 4.44 seconds. The reaction product is condensed. 57g of condensate are obtained, which consists of 25.3 g of indole, 1.0 of methyl indoles and 29.4 g of unconverted o-ethylaniline.

The indole yield related to the converted o-ethylaniline amounts to 84.2% of the theoretical yield.

EXAMPLE 2

60.5 g (½ mole) o-ethylaniline are fed within 2 hours into an evaporator by means of a metering pump, and evaporated. At the same time, 67.2 Nl hydrogen are fed by a metering apparatus to the preheat zone of a glass reactor, where mixing with the o-ethylaniline vapors at a temperature of 500° C occurs.

The gas mixture is contacted in the reactor with 100 ml of an Al$_2$O$_3$-containing catalyst heated to 550° C. The catalyst is previously modified with 21.4% by weight of chromium dioxide and 0.4% by weight copper.

The space velocity is 392h$^{-1}$, the time of direct contact is 2.25 seconds. The reaction product is condensed. 49.5 g of condensate are obtained, which consists of 32.9 g of indole, 3.1g of methyl indoles, 5.5g of aniline and 3.1g of unconverted o-ethylaniline.

The indole yield related to the converted o-ethylaniline amounts to 59.3% of the theoretical yield.

As previously indicated, the catalyst employed in practicing the process of this invention contains at least about 15% by weight copper. Generally speaking, the upper limit to the amount of copper employed in the catalyst is not critical. Typically, the amount of copper in the catalyst will be about 15 – 35% by weight.

Similarly, it was previously indicated that the amount of the chromate of the metal of Group IIA is at least about 8% by weight of the catalyst. While the upper limit of the amount of the chromate is not generally critical, the amount of chromate will typically be about 8 – 25% by weight.

It will be apparent from the two Examples that the process of this invention affords very good indole yields in glass apparatus; only a few side products are formed. In steel apparatus, however, only about 15% lower yield could be obtained, and the split product fraction (aniline, toluidine, etc.) was substantially greater. Aniline selectivity in steel was found to be 15.6% as compared to 1.4% in glass, and o-toluidine selectivity in steel was 10.9% as opposed to 1.2% in glass. It was also found that o-ethylaniline in the presence of hydrogen in a steel tube heated to 560° C (without catalyst) decomposes to a certain extent, which does not occur at all with the same conditions in a glass tube.

It has now been found that equally good yields in steel apparatus, as in glass, can be obtained if the process of this invention is conducted in the presence of steam instead of hydrogen, with a molar ratio of O-ethylaniline to steam of 1:6 to 1:24.

Thus, in another embodiment of this invention, the process of this invention is conducted in the presence of steam in steel apparatus rather than in the presence of hydrogen in glass apparatus.

DT-OS No. 2 148 961 (published Apr. 6, 1972) discloses the preparation of indole by the conversion of o-ethylaniline at 560° C in the presence of air and moisture. The DT-OS does not, however, disclose the catalyst employed in the process of this invention.

In the embodiment of this invention in which steam is employed, selectivities for indole of 87.1%, for aniline of 1.9% and for o-toluidine of 2.9% were found.

It has been observed that o-amino-styrene occurs as a side product in the process of this invention; it is readily converted to indole. Thus, according to another preferred embodiment of this invention, o-amino styrene is recycled to the process.

The following Examples demonstrate the use of steam in steel apparatus.

EXAMPLE 3

In a reactor consisting of Cr-Ni tubes having 32 mm diameter, there is introduced into each steel tube 800 ml of a SiO$_2$ catalyst modified with 22% by weight copper, 8% by weight barium chromate and 2% by weight chromium dioxide, in the form of strands (4 mm diameter × 4 to 7 mm) over a length of 800 mm. The catalyst is then treated at a temperature of 200° to 300° C for about 3 hours with a hydrogen/nitrogen mixture, and after cutoff of the gas flow the reactor is heated to 570° C.

At atmospheric pressure, by means of a pair of dispensing pumps, 12.1 parts by weight o-ethylaniline and 10.8 parts by weight water (molar ratio 1:6) are fed within 1 hour into an evaporator and vaporized at 300° C. The gas mixture is then continuously fed to the reactor via a preheater heated to 570° C.

Reaction conditions are: volume rate 196 h$^{-1}$, residence time 4.44 sec and flow speed 16.7 cm/sec.

The resulting reaction mixture is condensed, and after separation of the water/oil phases, the aqueous phase is returned to the reactor and the oily phase is fractionated in a lateral flow column.

While essentially an unreacted mixture of o-ethylaniline and o-amino styrene is obtained as head product, which mixture is returned to the reactor, indole is separated off at the lower part of the column.

From 12.1 parts by weight o-ethylaniline, 8.85 parts by weight indole are obtained in a purity of 99%, which corresponds to an indole selectivity of 75.5%. The o-ethylaniline conversion is 62.2%. Indole yield is 47.0%. The selectivities of o-toluidine and aniline are 5.1% and 4.9%, respectively. Losses amount to 14.5%.

EXAMPLE 4

At atmospheric pressure, with use of a pair of dispensing pumps, 12.1 parts by weight o-ethylaniline and 10.8 parts by weight water (molar ratio 1:6) are fed in the course of one hour into an evaporator and vaporized at 290° C. The gaseous mixture then passes continuously via a preheated heated to 560° C. into the reactor of Example 3, heated to 560° C (the reactor filled with the catalyst described in Example 3).

Reaction conditions are: volume rate 196 h$^{-1}$, residence time 4.5 sec and flow speed 16.7 cm/sec.

After workup of the condensate as described in Example 3, 10.2 parts by weight indole are obtained from 12.1 parts by weight o-ethylaniline, corresponding to an indole selectively of 87.1%. The o-ethylaniline conversion is 52.1%. Indole yield: 45.4%. The selectivity of o-toluidine and aniline are 2.9% and 1.9%, respectively. Losses amount to 8.1%.

What is claimed is:

1. A process comprising catalytically converting o-ethylaniline to indole in a gaseous phase and in the presence of hydrogen or steam and an SiO$_2$-containing catalyst modified by chromium dioxide and copper, said conversion conducted at about 400°–700° C, wherein said catalyst consists essentially of about 55-65% by weight SiO$_2$, about 18-24% by weight copper, about 8-10% by weight barium chromate, and about 2-4% by weight chromium dioxide.

2. A process according to claim 1 in which the reaction temperature is about 500° – 600° C.

3. A process according to claim 1 in which o-ethylaniline and hydrogen are present in the gaseous phase in a mole ratio of o-ethylaniline to hydrogen of about 1:4 – 1:20.

4. A process according to claim 1 in which o-ethylaniline and hydrogen are present in the gaseous phase in a mole ratio of o-ethylaniline to hydrogen of about 1:4 – 1:8.

5. A process according to claim 1 wherein the reaction temperature is about 500° – 600° C, and wherein o-ethylaniline and hydrogen are present in the gaseous phase in a mole ratio of o-ethylaniline to hydrogen of about 1 : 4 to about 1 : 8.

6. A process according to claim 1 in which o-ethylaniline and steam are present in the gaseous phase in a mole ratio of o-ethylaniline to steam of about 1:6 – 1:24.

7. A process according to claim 6 in which the reaction temperature is about 500° – 600° C.

8. A process according to claim 6 in which the reaction temperature is about 560° – 570° C.

9. Process according to claim 6 in which any o-amino styrene obtained is recycled to said process.

* * * * *